(12) United States Patent
Greener

(10) Patent No.: US 9,504,421 B2
(45) Date of Patent: Nov. 29, 2016

(54) MOISTURE INDICATING HYDROPHILIC POLYURETHANE

(71) Applicant: ACTIVE DEVICE DEVELOPMENT LIMITED, York (GB)

(72) Inventor: Bryan Greener, Yorkshire (GB)

(73) Assignee: MÖLNLYCKE HEALTH CARE AB, Göteborg (SE)

( * ) Notice: Subject to any disclaimer, the term of this patent is extended or adjusted under 35 U.S.C. 154(b) by 0 days.

(21) Appl. No.: 14/441,667

(22) PCT Filed: Nov. 12, 2013

(86) PCT No.: PCT/GB2013/052982
§ 371 (c)(1),
(2) Date: May 8, 2015

(87) PCT Pub. No.: WO2014/076467
PCT Pub. Date: May 22, 2014

(65) Prior Publication Data
US 2015/0272495 A1 Oct. 1, 2015

(30) Foreign Application Priority Data

Nov. 14, 2012 (GB) .................................. 1220481.4

(51) Int. Cl.
*A61F 13/00* (2006.01)
*A61F 13/42* (2006.01)
(Continued)

(52) U.S. Cl.
CPC ............... *A61B 5/443* (2013.01); *A61B 5/742* (2013.01); *A61F 13/00055* (2013.01);
(Continued)

(58) Field of Classification Search
CPC .. A61F 13/00; A61F 13/00055; A61F 13/42; A61F 13/422; A61F 2013/422; A61F 2013/42; G01N 31/22; G01N 31/222; G01N 3/22; A61L 15/56
USPC .......................... 503/214, 221; 600/306, 584
See application file for complete search history.

(56) References Cited

U.S. PATENT DOCUMENTS 3,635,652 A 1/1972 Streck
3,661,860 A 5/1972 Schwarz
(Continued)

FOREIGN PATENT DOCUMENTS

CN 101522149 A 9/2009
DE 10115004 A1 10/2002
(Continued)

OTHER PUBLICATIONS

White et al., Journal of Materials Science, 2005, 40, 669.
(Continued)

*Primary Examiner* — Bruce H Hess
(74) *Attorney, Agent, or Firm* — Ballard Spahr LLP

(57) ABSTRACT

The present invention relates at least in part to devices which are capable of indicating the presence of moisture. Embodiments of the present invention involve the provision of a solid dispersion of a color-forming material in a hydrophilic polyurethane material. In particular, although not exclusively, the present invention relates to devices comprising foam, e.g., hydrophilic polyurethane foam and a color former. Also included in the embodiments of the present invention are methods comprising the use of the devices, and other subject matter.

33 Claims, 13 Drawing Sheets

(51) Int. Cl.
- *G01N 31/22* (2006.01)
- *A61L 15/56* (2006.01)
- *A61B 5/00* (2006.01)
- *C08G 18/76* (2006.01)
- *C09D 7/00* (2006.01)
- *C08K 5/00* (2006.01)
- *A61L 15/26* (2006.01)
- *B05D 1/02* (2006.01)
- *B05D 1/18* (2006.01)
- *B05D 1/28* (2006.01)
- *B05D 3/02* (2006.01)
- *B05D 3/04* (2006.01)
- *C08G 18/08* (2006.01)
- *C08J 9/36* (2006.01)
- *C08K 5/18* (2006.01)
- *C08G 101/00* (2006.01)

(52) U.S. Cl.
CPC ........ *A61F 13/00068* (2013.01); *A61F 13/42* (2013.01); *A61L 15/26* (2013.01); *A61L 15/56* (2013.01); *B05D 1/02* (2013.01); *B05D 1/18* (2013.01); *B05D 1/28* (2013.01); *B05D 3/0254* (2013.01); *B05D 3/0493* (2013.01); *C08G 18/14* (2013.01); *C08G 18/7621* (2013.01); *C08G 18/7657* (2013.01); *C08G 18/7664* (2013.01); *C08J 9/365* (2013.01); *C08K 5/0041* (2013.01); *C08K 5/18* (2013.01); *C09D 7/007* (2013.01); *G01N 31/222* (2013.01); *A61B 2560/0412* (2013.01); *A61F 2013/422* (2013.01); *C08G 2101/00* (2013.01); *C08J 2201/036* (2013.01); *C08J 2207/10* (2013.01); *C08J 2375/04* (2013.01); *C08K 2201/013* (2013.01)

(56) References Cited

U.S. PATENT DOCUMENTS

| | | | |
|---|---|---|---|
| 5,399,609 | A | 3/1995 | Moss |
| 7,913,640 | B2 | 3/2011 | MacDonald et al. |
| 8,080,704 | B2 * | 12/2011 | Uchida ............. A61L 15/56 604/361 |
| 2006/0142529 | A1 | 6/2006 | Thiede et al. |
| 2007/0207925 | A1 | 9/2007 | Benkhoff et al. |
| 2009/0326494 | A1 | 12/2009 | Uchida et al. |
| 2011/0144603 | A1 | 6/2011 | Song |
| 2012/0143160 | A1 | 6/2012 | Song |
| 2012/0165771 | A1 * | 6/2012 | Ruman ............. A61F 13/42 604/361 |

FOREIGN PATENT DOCUMENTS

| | | |
|---|---|---|
| GB | 2410748 A | 8/2005 |
| WO | WO-8300742 A1 | 3/1983 |
| WO | WO-2011049522 A1 | 4/2011 |

OTHER PUBLICATIONS

International Search Report by the International Searching Authority mailed on May 22, 2014, for international application PCT/GB2013/052982 filed on Nov. 12, 2013, and published as WO 2014/076467 on May 22, 2014 (4 pages).

* cited by examiner

MOISTURE INDICATING HYDROPHILIC POLYURETHANE

CROSS-REFERENCE TO RELATED APPLICATIONS

The present application is a U.S. National Phase Application of International Application No. PCT/GB2013/052982, filed Nov. 12, 2013, which claims priority to Great Britain Patent Application No. 1220481.4, filed Nov. 14, 2012, each of which are hereby incorporated by reference in their entirety.

FIELD OF THE INVENTION

The present invention relates at least in part to devices which are capable of indicating the presence of moisture. Embodiments of the present invention involve the provision of a solid dispersion of a colour-forming material in a hydrophilic polyurethane material. In particular, although not exclusively, the present invention relates to devices comprising foam, e.g. hydrophilic polyurethane foam and a colour former. Also included in embodiments of the present invention are methods using the devices, and other subject matter.

BACKGROUND TO INVENTION

Hydrophilic polyurethane (HPU) foams are employed in a range of applications including medical applications. Medical HPU foams are commonly manufactured from an oligomeric urethane-ether pre-polymer, water and a surfactant (see *Design and Applications of Hydrophilic Polyurethanes*, T. Thomson, CRC Press, 2000). The urethane-ether prepolymer is commonly based upon one of two isocyanate pre-cursors: methylene diphenyl diisocyanate (MDI) or toluene diisocyanate (TDI). HPU foams are able to absorb many times their own weight in water-based liquids, including human serum, without significant visible change in appearance; this can make it difficult for a user or carer to assess how wet a HPU device is in situ in use. Whilst moist wound healing is the current paradigm for wound care, a wound dressing that is wet or moist can incubate bacterial growth and/or cause maceration of the periwound and this is detrimental to wound healing. Thus, there is a need to visualise the location and extent of moisture and liquid in HPU-based medical devices. This need is not restricted to HPU-based devices or medical devices.

Colour-formers or colour forming materials are chemicals that can exist in two or more coloured states, one of which may be colourless. The transition between coloured states is achieved by a change in the environment of the colour-former (CF); this can, for example, be a change in pressure, temperature, light intensity or solvent. In each of these cases, the CF requires custom formulation with other excipients to respond to each specific environmental change. In general, different excipients are required to translate different environmental stimuli into a change in the coloured state of the CF. Thus, the same CF can be employed in a range of colour-indicating applications for a variety of environmental changes.

The prior art includes materials which take on the colour of a fluid to which they are exposed, see for example WO2011/049522. These materials are not examples of a colour-forming material but, rather, are coloured, absorbent materials.

Known thermochromic CF systems typically rely upon a highly specific set of excipients. The excipient-specificity of one such system is investigated and demonstrated by White et al in Journal of Materials Science, 2005, 40, 669.

Moisture-indicating CF systems are reported in the prior art but they are unsatisfactory for a number of reasons, primarily because one or more of the components of each system is water-soluble; thus the indicating system can be washed-out from its intended location. This is unsuitable for most medical and household applications.

U.S. Pat. No. 7,913,640 discloses a system for indicating the presence of moisture (but not humidity) in heat and moisture exchange (HME) devices. The indicating system comprises an intimate mixture of CF and an activator that, in the absence of moisture, is colourless but, when exposed to moisture, becomes coloured to an extent that can easily be observed by eye. An example of an indicating system is a mixture of the CF crystal violet lactone and the activator 2-sulfosalicylic acid. The presence of moisture solubilises the activator and allows it to interact with the CF, resulting in colour formation.

US Patent Publication No. 2011/0144603 discloses a wetness indicating system for use in a range of absorbent devices. The system described relies upon four components: a leuco dye (CF), a colour developer (activator), a separator and an encapsulation matrix. The system is colourless in the dry state and becomes strongly coloured when wet due to the dissolution of the separator. Once again, this is undesirable for direct medical usage. The examples disclosed in US Patent Publication No. 2011/0144603 become coloured when wet and remain coloured when re-dried due to wash-out of the separator.

The minimum requirement for colour formation in any of the systems described above is a CF and an activator. For example, Ichimura et al describe the solid-state adsorption of crystal violet lactone (CF) on silica nanoparticles (activator) to generate strongly coloured products in Langmuir, 2008, 24(13), 6470-6479; demonstrating that a solvent is not a pre-requisite for such interactions.

The colour former crystal violet lactone is applied in a range of colour-indicating applications that rely upon its property of reversible colour change. The compound exists in its isolated pure state as an off-white lactone. In the presence of selected molecules or surfaces of appropriate charge or structure (activators), the lactone form of the molecule transforms to its charged, highly coloured leuco form.

GB2410748 and U.S. Pat. No. 3,635,652 discuss that polyurethane-based materials can be loaded with therapeutic agents or dyestuffs respectively. None of these agents or dyestuffs are colour forming species. U.S. Pat. No. 5,399,609 teaches that water-soluble moisture indicating particles (transition metal salts) can be mixed with thermoplastic polyurethane resins to indicate the moisture level in the material. The metal salts are immiscible with the polyurethane resin and remain particulate. Metal salts are not examples of colour forming materials.

US2012/0143160 discusses that colour forming systems comprising multiple components, at least some of which are water soluble, can be rendered less water soluble by entrapment in a water insoluble but water-permeable matrix.

Moreover, the inventor is not aware of prior art that discloses or anticipates the molecular dispersion or partial molecular dispersion of a colour former in a hydrophilic polyurethane for the indication of wetness.

It is an aim of the present invention to at least partly mitigate the problems associated with the prior art.

It is an aim of certain embodiments of the present invention to create a moisture-indicating system which is suitable for use in topical or penetrating medical devices or other non-medical devices.

It is an aim of certain embodiments of the present invention to provide a solid dispersion of a colour-forming material in a hydrophilic polyurethane for use to indicate wetness e.g. moisture.

It is an aim of certain embodiments of the present invention, to provide a system wherein none of the interacting species (e.g. pre-colorant, activator, solvent or separator) are solubilised when moisture is absorbed, thereby eliminating the risk of release of any of these species into the local environment of the device.

It is an aim of certain embodiments to provide a molecular dispersion or partial molecular dispersion of a colour-forming material in a hydrophilic polyurethane.

Furthermore, it is an aim of certain embodiments of the present invention to generate a moisture-indicating system that responds in a proportional colour-intensity manner to moisture level. In contrast, the prior art generate a step-change colour response.

It is an aim of certain embodiments of the present invention to generate a moisture-indicating system that is capable of reversible moisture indication.

Furthermore, it is an aim of certain embodiments of the present invention to generate a moisture-indicating system that is substantially colour-stable in moist and wet environments for periods of at least 24 hours.

Furthermore, it is an aim of certain embodiments of the present invention to generate a moisture-indicating system that is substantially stable following sterilisation.

Furthermore, it is an aim of certain embodiments of the present invention to generate a moisture-indicating system that is substantially light-stable.

SUMMARY OF CERTAIN EMBODIMENTS OF THE INVENTION

Certain embodiments of the present invention are based on the provision of a material comprising a solid dispersion of a colour-forming material in a hydrophilic polyurethane.

Certain embodiments of the present invention relate to a material comprising a molecular dispersion or partial molecular dispersion of a colour-forming material in a hydrophilic polyurethane.

Aptly, the dispersion is for use to indicate wetness or moisture. In one embodiment, the hydrophilic polyurethane is a continuous phase. In one embodiment, the colour-forming species is a dispersed phase. The colour-forming species may be a fully dispersed phase or a partially dispersed phase.

Certain embodiments of the present invention relate to devices comprising a solid dispersion of a colour-forming material in a hydrophilic polyurethane for indicating moisture or wetness level.

Certain embodiments of the present invention relate to devices comprising a molecular dispersion or partial molecular dispersion of a colour-forming material in a hydrophilic polyurethane for indication of moisture or wetness level.

Certain embodiments of the present invention relate at least in part to devices comprising colour-forming dyes and hydrophilic polyurethane (HPU) foams which respond in a proportional colour-intensity fashion to absorbed moisture. Aptly, the system requires no addition excipients to function successfully. Without being bound by theory, it is believed that, in its hydrated state, the HPU foam acts as an activator for the colour-forming dye, while in its dry state, it does not. Neither the HPU foam nor an appropriate colour-forming dye are significantly soluble in aqueous media and thus present a low safety risk in use.

Furthermore, without being bound by theory, it is believed that the ability of HPU foam to absorb both aqueous and organic liquids enables the preparation of the materials of certain embodiments of the present invention. It is considered that colour-forming species may not be prepared as solid dispersions within materials that are not solvated by organic solvents in which colour formers may be solubilised.

Aptly, the article is a reversible moisture indicator, that is to say, the colour former reverts back to its original colour as the moisture level of a target location which is situated at or proximate to the article reduces. In certain embodiments of the present invention, the article may be capable of repeated changes from an original colour state to a second colour state and back to the original colour state as moisture levels alter.

Aptly, the article can be used to quantify in a proportional manner moisture levels of a target location which is situated at or proximate to the article.

In a first aspect of the present invention, there is provided an article for indicating presence of moisture comprising a material comprising a hydrophilic polyurethane and a colour-forming species.

Aptly, the hydrophilic polyurethane and/or colour-forming species is substantially insoluble in an aqueous medium.

Aptly, the hydrophilic polyurethane is a hydrophilic polyurethane foam.

Aptly, the hydrophilic polyurethane foam is formed from a composition comprising a prepolymer based on: methyl diphenyl diisocyanate, toluene diisocyanate, hexane diisocyanate, hydrogenated methyl diphenyl diisocyanate, isopherone diisocyante, or naphthalene diisocyanate.

Aptly, the hydrophilic polyurethane is formed from a composition comprising at least 1% by weight of a methyl diphenyl diisocyanate (MDI)-based prepolymer.

Aptly, the MDI-based prepolymer comprises 5-90% by weight of MDI. More aptly, the MDI-based prepolymer comprises 10-50% by weight of MDI.

Aptly, the hydrophilic polyurethane is formed from a composition comprising at least 1% by weight of a toluene diisocyanate (TDI)-based prepolymer.

Aptly, the TDI-based prepolymer comprises 5-90% by weight of TDI. More aptly, the TDI-based prepolymer comprises 10-50% by weight of TDI.

Aptly, the colour-forming species is a molecule which can exist in at least two coloured states, wherein the species exists in one of the coloured states when in contact with moisture. In one embodiment, the colour-forming species is an organic molecule.

Aptly, one of the coloured states is a colourless state.

In one embodiment, the colour-forming species is a colour-forming dye. Aptly, the colour-forming dye is a phthalide-based leuco dye. Aptly, the colour-forming dye is crystal violet lactone (as shown in FIG. 1). Aptly, the colour-forming dye has a structure as shown in FIG. 3. Details of additional suitable colour-forming dyes which may be used in embodiments of the present invention are provided herein.

In one embodiment, the article comprises a plurality of colour-forming species. Aptly, each colour-forming species of the plurality of colour-forming species is provided in discrete regions of the article. In one embodiment, the article comprises a mixture of colour forming species.

Aptly, the colour forming species is loaded onto the hydrophilic polyurethane at a level of about 10% w/w or lower, e.g. about 1% w/w or lower.

Aptly, the colour-forming species is coated on a surface of the hydrophilic polyurethane. Such a surface coating is taken to mean any depth in the range 0-5 mm from the outside of the article.

In one embodiment, the article comprises a pattern comprising the colour-forming species.

Aptly, the article does not comprise an excipient.

In a further aspect of the present invention there is provided a device for indicating the presence of moisture at a site, wherein the device comprises an article as described herein.

Aptly, the device is for topical application to a site on a subject.

In one embodiment, the device further comprises a protective layer on a surface thereof. Aptly, the protective layer is provided adjacent to the surface on which the colour forming species is coated.

In one embodiment, the device is for medical use. Aptly, the device is adapted to be applied to a wound or other penetrating site.

Aptly, the device comprises an inlet and an outlet and is for the exchange of heat and moisture.

Aptly, the device is for use in an artificial respiratory system.

In a further aspect of the present invention, there is provided a method of manufacturing an article as described herein, the method comprising:
 a) forming a solution of a colour forming species in a non-aqueous solvent;
 b) combining the solution of (a) with a hydrophilic polyurethane; and
 c) removing the non-aqueous solvent.

Aptly, combining the solution with a hydrophilic polyurethane comprises spray-coating, dipping and/or printing. Aptly, removing the non-aqueous solvent comprises heating the article and/or applying a reduced pressure thereto and/or evaporating the solvent at ambient temperature (e.g. about 18-25° C.). Aptly, the non-aqueous solvent is selected from an organic solvent or a slightly polar solvent.

Aptly, the non-aqueous solvent is selected from acetone, xylene, toluene, iso-propanol, ethanol and methanol or combinations of the aforementioned solvents.

In a further aspect of the present invention, there is provided a method of detecting moisture in a target location comprising locating the article as described herein or a device as described herein at or proximate to the target location.

Aptly, the method comprises detecting whether the article and/or device has undergone a colour change.

Aptly, the method further comprises comparing a colour change of the article and/or device with a calibrated colour chart.

Aptly, the method further comprises measuring the colour change of the article and/or device with a spectrometer.

In a further aspect of the present invention, there is provided a material comprising a solid dispersion of a colour-forming species in a hydrophilic polyurethane. Aptly, the colour-forming species is as described herein. Aptly, the hydrophilic polyurethane is as described herein.

In a further aspect of the present invention, there is provided a material comprising a molecular dispersion or partial molecular dispersion of a colour-forming species in a hydrophilic polyurethane. Aptly, the colour-forming species is as described herein. Aptly, the hydrophilic polyurethane is as described herein.

In a further aspect of the present invention, there is provided a device comprising a solid dispersion of a colour-forming species in a hydrophilic polyurethane for indicating moisture or wetness level.

BRIEF DESCRIPTION OF THE DRAWINGS

Embodiments of the present invention will now be described in more detail below, by way of example only, with reference to the accompanying drawings, in which.

Figure 7:
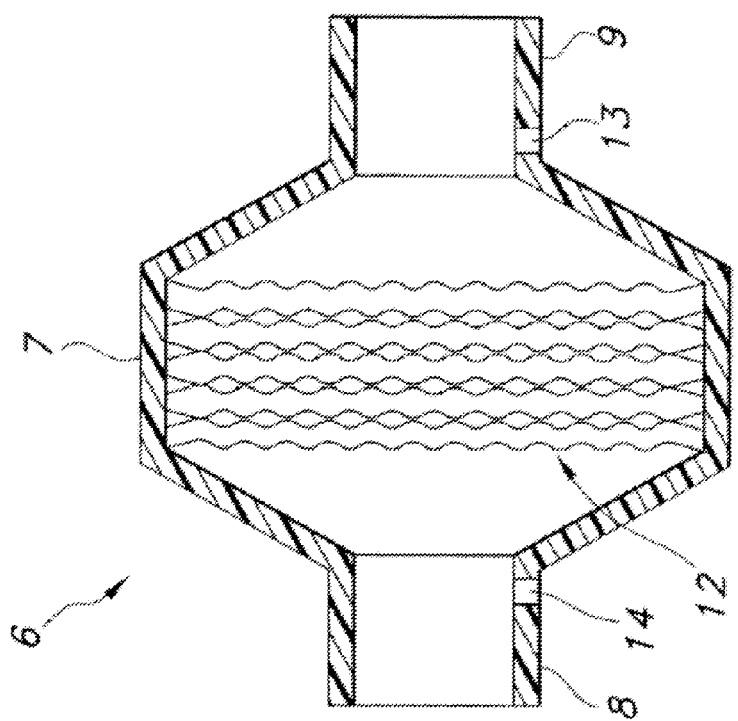
FIG. 7 is a cross-section view of a device (6) according to an embodiment which is for the exchange of heat and moisture (HME device). Aptly, the device has an inlet (8) with a tube insertion hole (14) and an outlet (9) with a tube insertion hole (13), an enlarged central portion (7) housing the heat and moisture exchange body (12) comprised of, or formed entirely of, a dry hydrophilic polyurethane foam layer with a single- or double-face coating of a colour-forming species.
Figure 8:
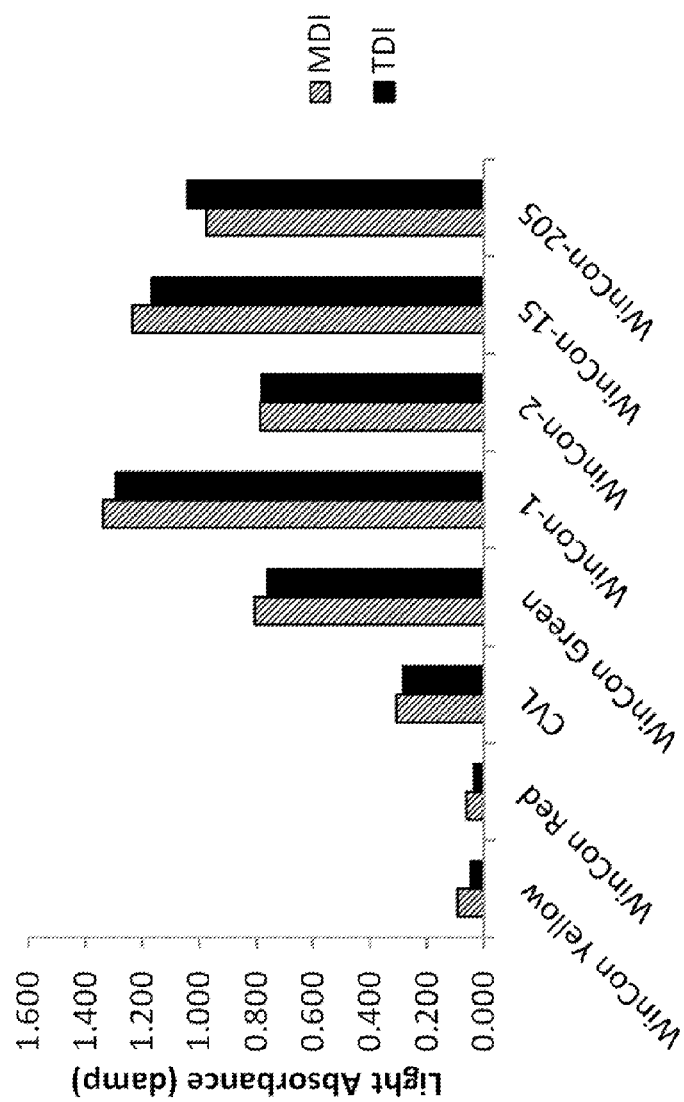
Figure 9:
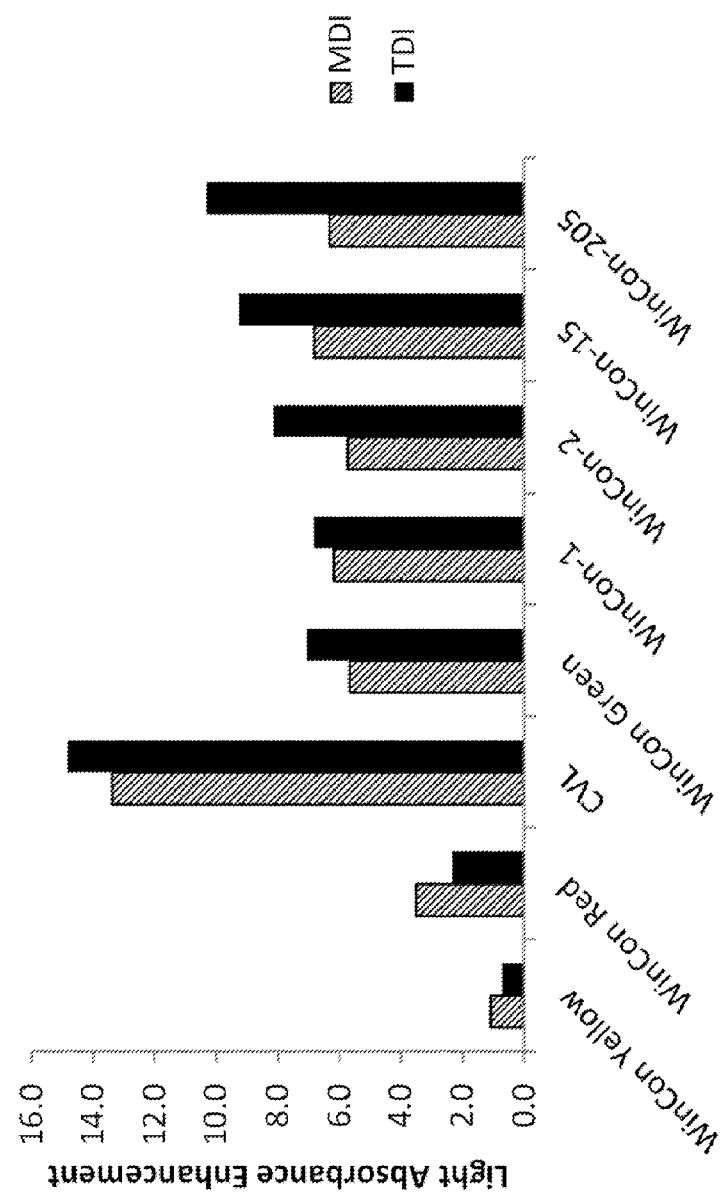
Figure 10:
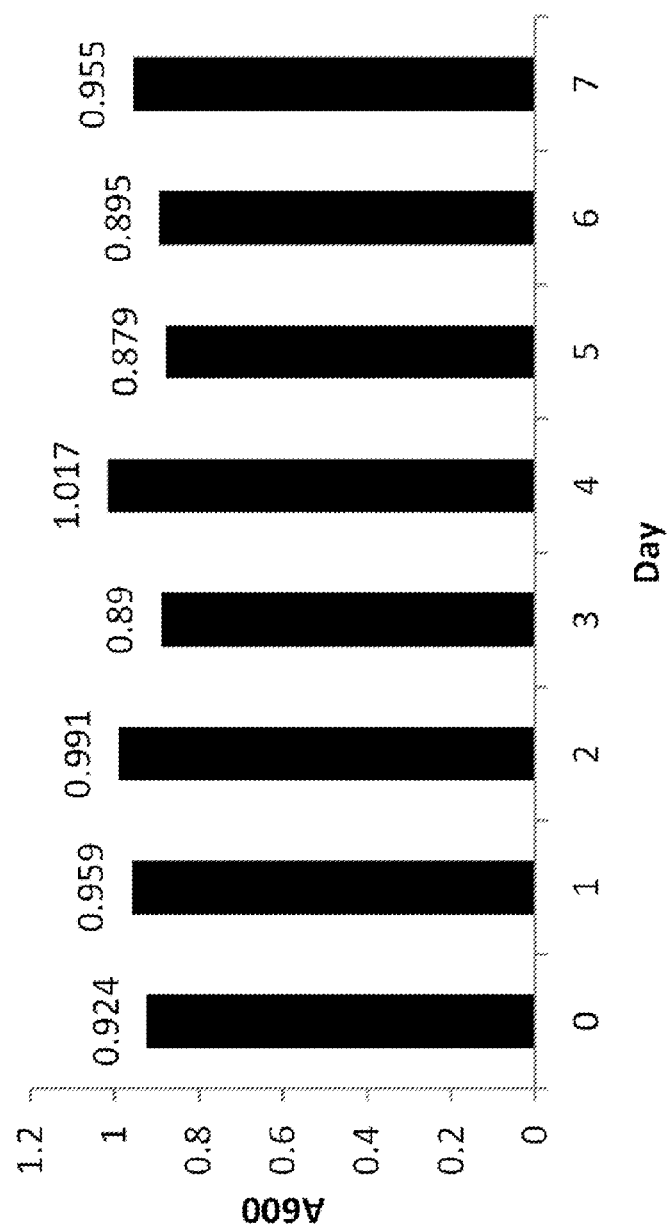
Figure 11:
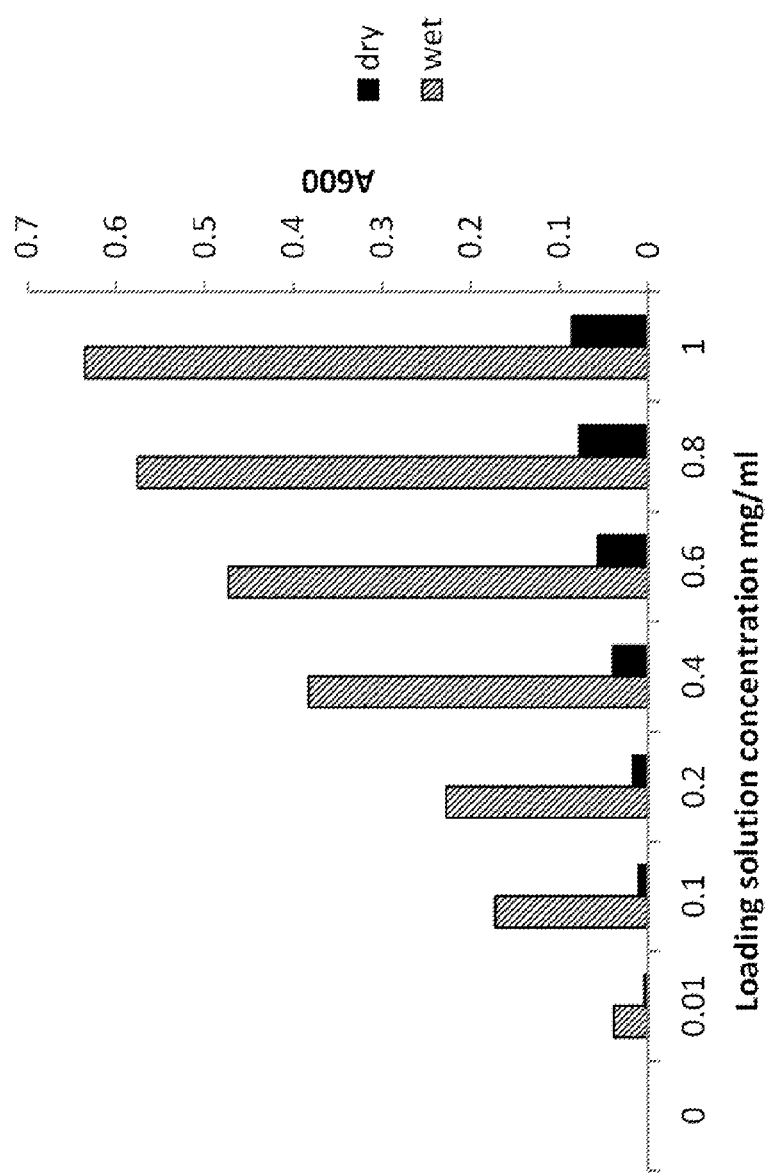
Figure 12:
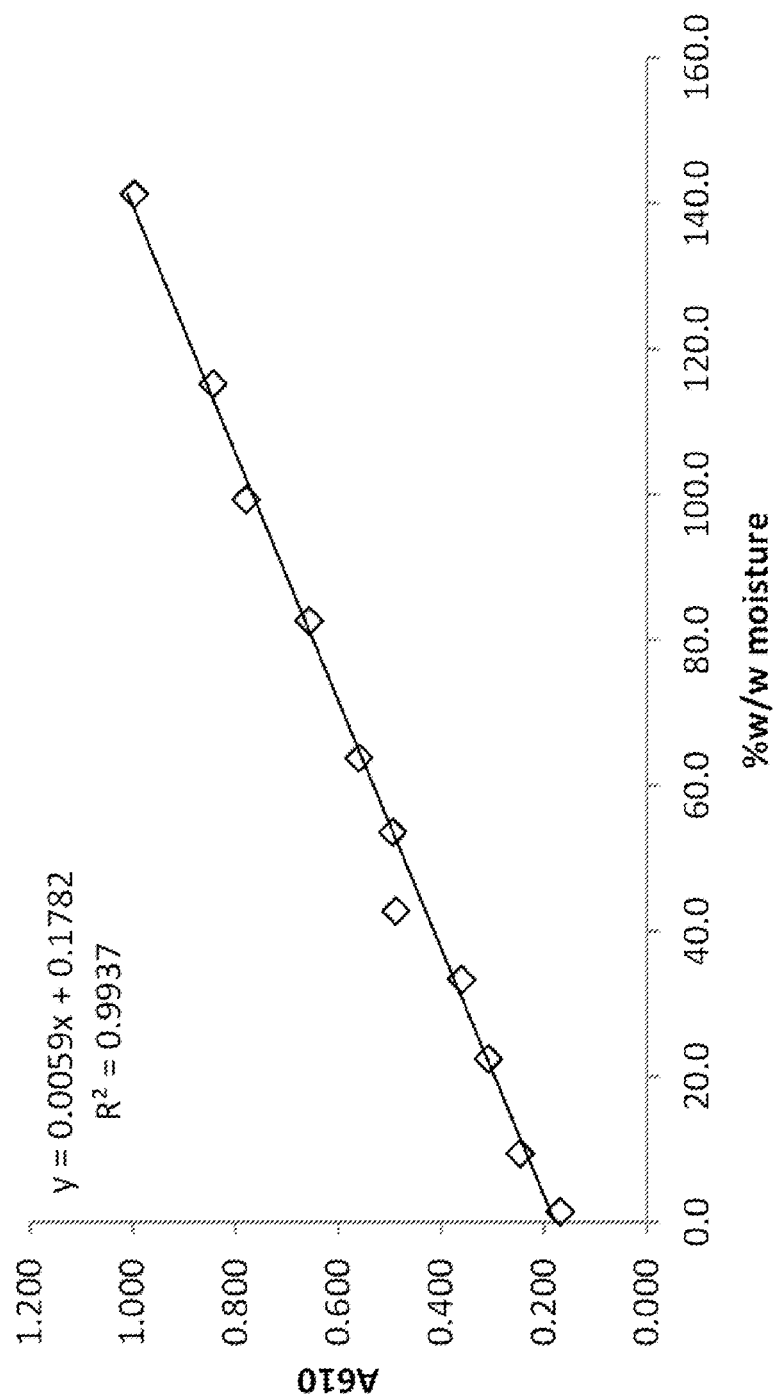

The device of FIG. 7 may be used as part of intubation devices for artificial respiration. Such devices are used during long-term ventilation and in sleep apnoea devices. In both cases, a HME chamber may be included in the tube-set of the apparatus to exchange heat and moisture on inhale-exhale. In the absence of this device, the windpipe can dry out and desiccate. Aptly, the HME device ensures that inhaled gas is humid;

FIG. 8 is a graph showing the light absorbances resulting from damp samples of Example 25;

FIG. 9 is a graph showing the light absorbance enhancement that results when samples are wet from dryness of Example 25;

FIG. 10 is a graph illustrating the results of Example 26;

FIG. 11 is a graph illustrating the results of Example 27;

FIG. 12 is a graph illustrating the results of Example 28; and

Figure 13:
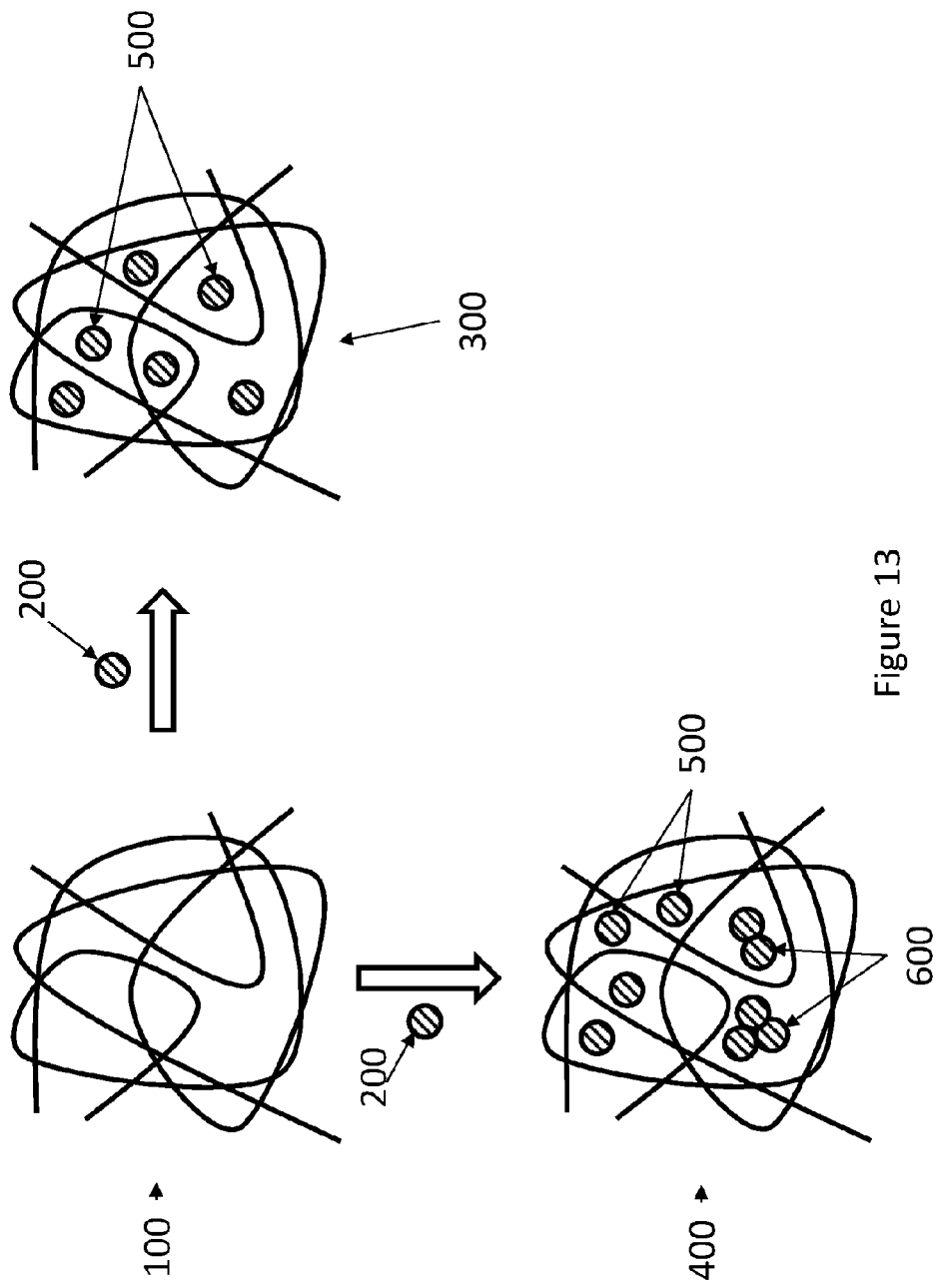

FIG. 13 is a schematic representation of a material of certain embodiments of the present invention. FIG. 13 shows a schematic polymer backbone structure of a hydrophilic polyurethane (100) and the addition of colour-forming molecules (200) to result in a solid dispersion that is either a molecular dispersion (300), consisting of isolated molecules of colour-former (500) dispersed within the hydrophilic polyurethane structure (100), or a partial molecular dispersion (400), consisting of some isolated molecules of colour-former (500) and some isolated molecular clusters of colour-former (600) dispersed within the hydrophilic polyurethane structure (100).

DETAILED DESCRIPTION OF CERTAIN EMBODIMENTS OF THE INVENTION

In a first aspect of the present invention, there is provided a material comprising a hydrophilic polyurethane (HPU) foam and a colour-forming species.

The term "hydrophilic polyurethane" as used herein is taken to mean a polyurethane material comprising at least 1% by weight of a urethane-ether prepolymer in its formulation.

Aptly, the material comprises a solid dispersion of a colour-forming species in a hydrophilic polyurethane material e.g. a hydrophilic polyurethane foam.

Aptly, the hydrophilic polyurethane foam is formed from a composition comprising a prepolymer based on: methyl diphenyl diisocyanate, toluene diisocyanate, hexane diisocyanate, hydrogenated methyl diphenyl diisocyanate, isopherone diisocyante, or naphthalene diisocyanate.

Aptly, the hydrophilic polyurethane comprises an MDI-based or TDI-based urethane-ether pre-polymer in its formulation. Aptly, the formulation comprises at least 5% by weight of an urethane-ether prepolymer e.g. 10%, 15% or greater.

Aptly, the hydrophilic polyurethane comprises at least 5% by weight of an MDI-based or TDI-based urethane-ether pre-polymer in its formulation e.g. 10%, 15% or greater.

Aptly, the hydrophilic polyurethane comprises a mixture of urethane-ether prepolymers.

Aptly, the hydrophilic polyurethane comprises a single urethane-ether prepolymer.

Aptly, the hydrophilic polyurethane comprises a mixture of an MDI-based pre-polymer and a TDI-based urethane-ether pre-polymer.

The term "MDI-based prepolymer" as used herein is taken to mean a material prepared from at least 1% by weight of a methyl diphenyl diisocyanate. Aptly, the term MDI-based prepolymer as used herein is taken to mean a material comprising 10-90% by weight of a methyl diphenyl diisocyanate. The remainder of the formulation may be a polyethylene oxide or polypropylene oxide polymer or a copolymer of the two.

The term "TDI-based prepolymer" as used herein is taken to mean a material prepared from at least 1% by weight of a toluene diisocyanate. Aptly, the term TDI-based prepolymer as used herein is taken to mean a material comprising 10-90% by weight of a toluene diisocyanate. The remainder of the formulation may be a polyethylene oxide or polypropylene oxide polymer or a copolymer of the two.

The term "MDI-based polyurethane" as used herein is taken to mean a polyurethane material comprising 1-80% by weight of a MDI-based urethane-ether pre-polymer in its formulation, e.g. 1%, 5%, 10%, 15%, 20%, 25%, 30%, 35%, 40%, 45%, 50%, 55%, 60%, 65%, 70%, 75% or 80%.

The term "TDI-based polyurethane" as used herein is taken to mean a polyurethane material comprising 1-80% by weight of a TDI-based urethane-ether pre-polymer in its formulation, e.g. 1%, 5%, 10%, 15%, 20%, 25%, 30%, 35%, 40%, 45%, 50%, 55%, 60%, 65%, 70%, 75% or 80%.

The term "methyl diphenyl diisocyanate" as used herein is taken to mean any geometric isomer of this compound and/or mixtures thereof.

The term "toluene diisocyanate" as used herein is taken to mean any geometric isomer of this compound or mixtures thereof.

The MDI-based polyurethane is aptly a hydrophilic polyurethane foam produced from a reaction of a MDI-based polyurethane pre-polymer and water in the presence of a surfactant.

The TDI-based polyurethane is aptly a hydrophilic polyurethane foam produced from a reaction of a TDI-based polyurethane pre-polymer and water in the presence of a surfactant.

Aptly, the hydrophilic polyurethane foam comprises a mixture of urethane-ether prepolymers.

Aptly, the hydrophilic foam may comprise a polyurethane which is based on a mixture of MDI and TDI.

Suitable MDI-based prepolymers include for example IP series (ITWC Inc., now BASF), Suprasec 2054, 2058 and 2059 (Huntsman Polyurethanes), Desmodur MDI-based prepolymers (Bayer), Hypol JM (Dow) and those described in US Patent Publication No. 2006/0142529 and the prior art described therein.

Suitable TDI-based prepolymers include, for example, Desmodur TDI-based prepolymers (Bayer), Lupranate TDI-based prepolymers (BASF) and Hypol JT (Dow).

The term "colour-forming species" as used herein is taken to mean a molecule that can exist in at least two coloured states, one of which may be colourless. Aptly, the colour forming species is an organic molecule.

Aptly, the colour-forming species is capable of forming a molecular dispersion or partial molecular dispersion in a hydrophilic polyurethane foam. Aptly, the colour-forming species forms a solid dispersion in a hydrophilic polyurethane foam.

Aptly, the material may be a powder e.g. a powder formed from cryo-milling of a HPU foam product. The powder may be incorporated into an article or product to indicate the presence of moisture.

The colour-forming species may be any known to the skilled artisan and may, for example, include: acyl auramines, acylleucophenothiazines, alpha- and beta-unsaturated aryl ketones, azaphthalides, basic mono azo dyes, 10-benzoyl-N,N,N',N'-tetraethyl-3,7-diamino-10H-phenoxazine, chromogenic azaphthalide compounds, diaryl phthalides, diphenylmethanes, dithio-oxamide, di[bis-(indolyl)ethylenyl]tetrahalophthalides, fluoran derivatives (3-dialkylamino-7-dialkylamylfluoran), 3-(indol-3-yl)-3-(4-substituted aminophenyl)phthalides, bis-(indolyl)ethylenes, indolyl red, leucoauramines, leucobenzoyl methylene blue, 3-methyl-2,2-spirobi(benzo-[f]-chromene), phenoxazine, phthalides including crystal violet lactone, malachite green lactone, phthalide red, phthalide violet, phthalans, benzoindolinospiropyrans, rhodamine beta lactams, spiropyrans, triphenylmethanes including gentian violet and malachite green.

The colour-forming species is aptly chosen from the following: leuco crystal violet [CAS 603-48-5], crystal violet lactone [CAS 1552-42-7], 7-Anilino-3-diethylamino-6-methyl fluoran [CAS 29512-49-0], 2-Anilino-6-dibutylamino-3-methylfluoran [CAS 89331-94-2], 3,3-bis(2-methyl-1-octyl-1H-indol-3-yl)-1(3H)-Isobenzofuranone [CAS 50292-95-0], N-ethyl-N-chloroethyl-3-toluidine [CAS 22564-43-8], N-ethyl-N-benzyl aniline-3'-sulfonic acid [CAS 101-11-1], 2-chlorobenzaldehyde oxime [CAS 3717-28-0], 6'-(diethylamino)-2'-[(dimethylphenyl)amino]-

Figure 2:
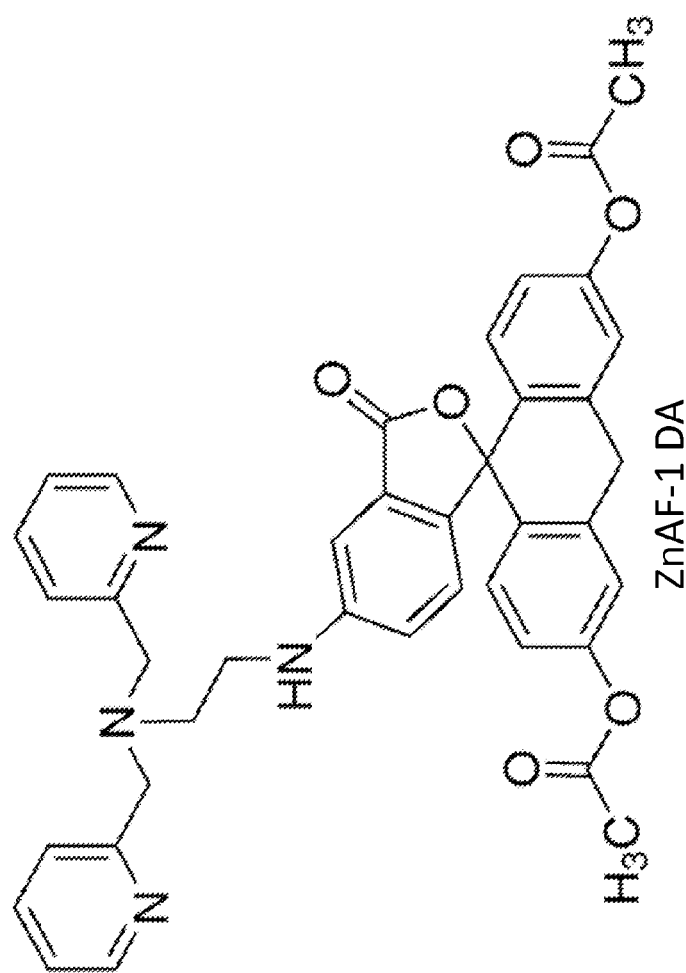
FIG. 2 illustrates the structure of a colour former of certain embodiments of the present invention, ZnAF-1 DA.

3'-methylspiro[isobenzofuran-1(3H),9'-[9H]xanthene]-3-one [CAS 72389-80-1], 3-(Ethylisoamylamino)-6-methyl-7-anilinofluoran [CAS 70516-41-5], 2'-(Dibenzylamino)-6'-(diethylamino)fluoran [CAS 34372-72-0], N,N-Dimethyl-4-[2-[2-(octyloxy)phenyl]-6-phenyl-4-pyridinyl]benzenamine [CAS 144190-25-0] or 4-[4-[4-[2-[4-[2-[4-(diethylamino)phenyl]quinazolin-4-yl]oxyphenyl]propan-2-yl]phenoxy]quinazolin-2-yl]-N,N-diethylaniline [CAS 90677-64-8], 3-(4-chloro-phenyl)-3-phenyl-3H-isobenzofuran-1-one; 10,10-dimethylspiro(anthracene-9(10H),1'(3'H)-isobenzofuran)-3'-one; 3-(2-(dimethylaminomethyl)phenyl)-3-phenylphthalide; (5,1',1',5")terisobenzofuran-1,3,3',1",3"-pentaone; 4-{1-[4-(benzoyloxy)phenyl]-3-oxo-1,3-dihydro-2-benzofuran-1-yl}phenyl benzoate; 3-(alpha-(4-chlorophenyl)-2-(dimethylamino)benzyl)-3-methylphthalide; o-Cresolphthalein Complexone [2411-89-4]; Fluorescein diacetate [596-09-8]; Naphthofluorescein [61419-02-1]; Fluorescein O,O'-diacrylate [7262-39-7]; Fluorescein o-acrylate [193419-86-2]; 5-Carboxyfluorescein diacetate [79955-27-4]; 3',6'-dichlorofluoran [630-88-6]; Rhodol [3086-44-0]; Fluorescein O,O'-dimethacrylate [206444-58-8]; Fluorescein O-methacrylate [480439-15-4]; Fluorescein dibutyrate [7298-65-9]; Fluorescein dilaurate [7308-90-9]; 2',7'-Dichlorofluorescein diacetate [2044-85-1]; Fluorescein diacetate 6-isothiocyanate; Rose Bengal diacetate [61738-01-0]; 3,4-diamino-9-(2-carboxyphenyl)-3,6-bis(diethylamino)xanthenium chloride, DAR-2 [261351-45-5]; 4,5-diamino-9-(2-carboxyphenyl)-3,6-bis(diethylamino)xanthenium chloride, DAR-1 [261351-43-3]; Eosin Y [15086-94-9]; Erythrosin B [15905-32-5]; Calcein [1461-15-0]; 4-nitrofluorescein [14926-29-5]; 2',7'-bis(2-Carboxyethyl)-5(6)-carboxyfluorescein acetoxymethyl ester Mixed isomers [117464-70-7]; Rose Bengal lactone [4159-77-7]; 2',4',5',7'-tetrabromo-3,4,5,6-tetrachlorofluorescein; Eosin diacetate [7284-92-6]; 5(6)-Carboxy-2',7'-dichlorofluorescein diacetate [127770-45-0]; 5(6)-Carboxyeosin diacetate [161338-87-0]; 5(6)-Carboxytetramethylrhodamine N-hydroxysuccinimide ester; Fluorescein Phosphoramidite; 6-FAM(R) [204697-37-0]; ZnAF-1 DA (as shown in FIG. 2); 5(6)-Carboxyfluorescein diacetate N-succinimidyl ester [150347-59-4]; 5(6)-Carboxy-X-rhodamine [198978-94-8] or a composition thereof.

Figure 1:
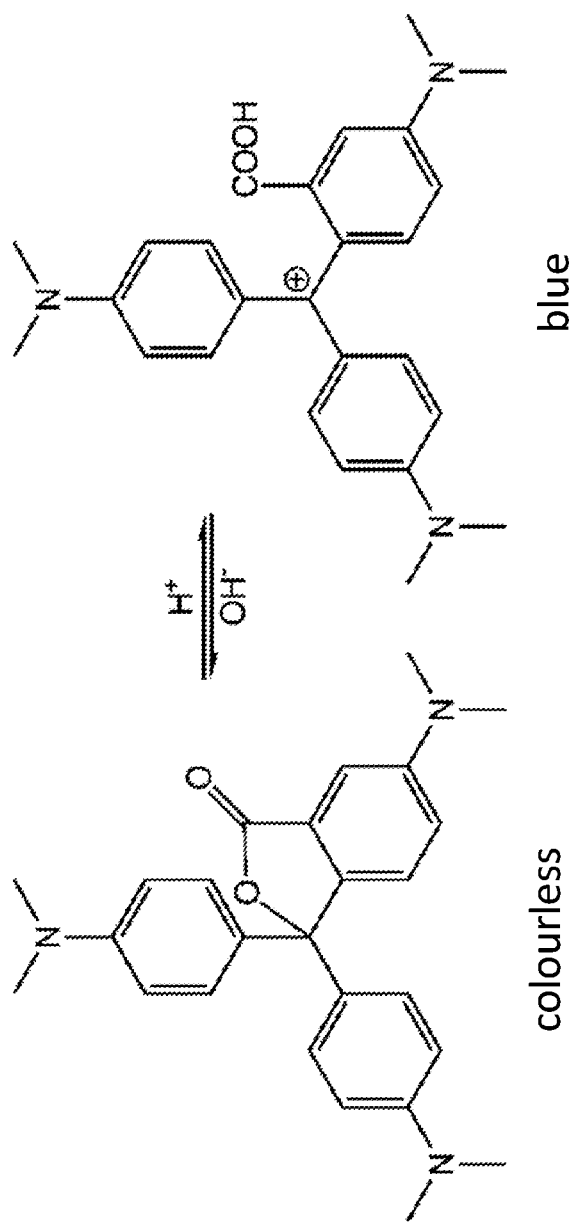
FIG. 1 illustrates the structure of crystal violet lactone in its colourless state and in its coloured state.
Figure 3:
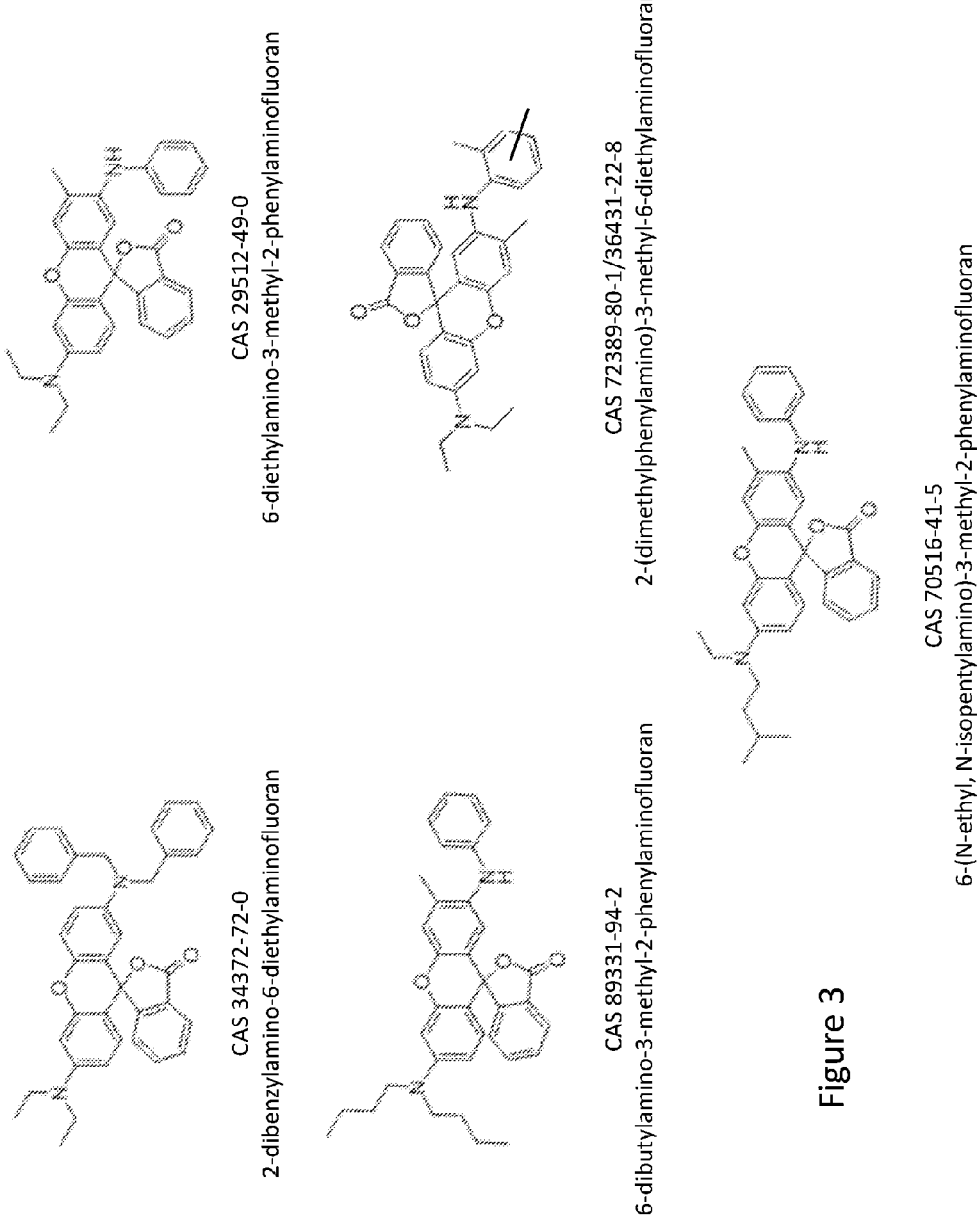
FIG. 3 illustrates the structure of various phthalide-based leuco dyes of certain embodiments of the present invention.
Figure 4:
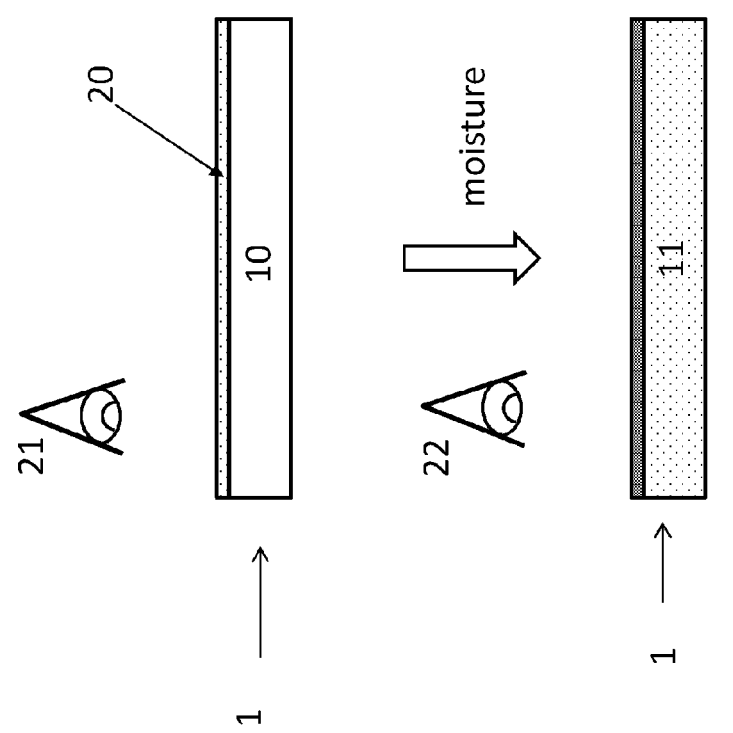
FIG. 4 illustrates a device (1) according to an embodiment in which a dry hydrophilic polyurethane foam (10) with a single-face coating of a colour-forming species (20) appears white (21) in the dry state and coloured (22) when moist (11)
Figure 5:
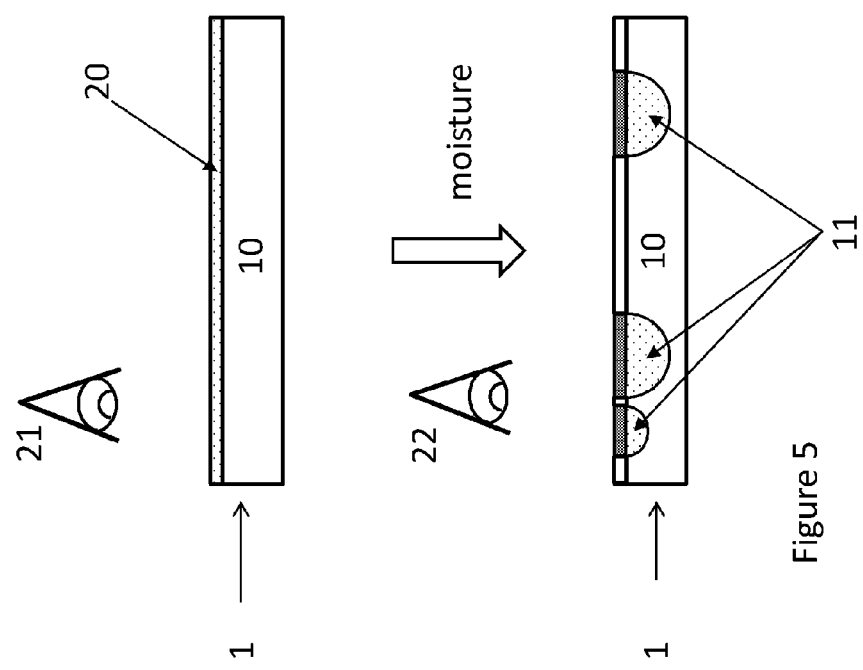
FIG. 5 illustrates a device (1) according to an embodiment in which a dry hydrophilic polyurethane foam (10) with a single-face coating of a colour-forming species (20) appears white (21) in the dry state and coloured (22) when moistened in specific locations (11)
Figure 6:
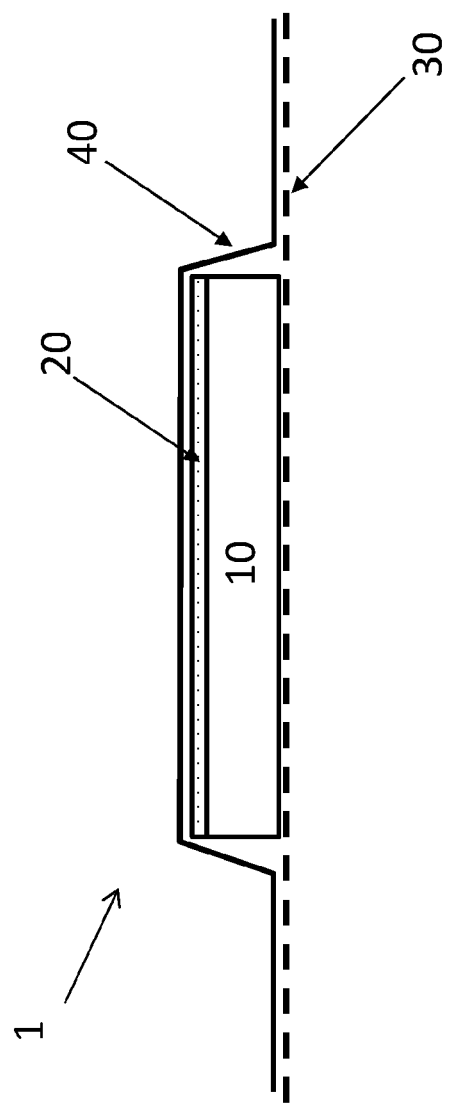
FIG. 6 illustrates a device (1) according to an embodiment which is for application to the surface of the skin comprising an adhesive or non-adhesive perforated layer (30), a dry hydrophilic polyurethane foam (10) layer with a single-face coating of a colour-forming species (20) and a surface film layer (40)

Aptly, the colour-forming species is a phthalide-based leuco dye chosen from the following: crystal violet lactone [CAS 1552-42-7], 6-diethylamino-3-methyl-2-phenylaminofluoran [CAS 29512-49-0], 2-Anilino-6-dibutylamino-3-methylfluoran [CAS 89331-94-2], 6-(N-ethyl,N-isopentylamino)-3-methyl-2-phenylaminofluoran [CAS 70516-41-5], 2-(dibenzylamino)-6-(diethylamino)fluoran [CAS 34372-72-0], 2-(dimethylphenylamino)-3-methyl-6-diethylaminofluoran [CAS 72389-80-1]. For the avoidance of doubt, these chemical structures are shown schematically in FIG. 1 and FIG. 3. The colour-forming species is also aptly chosen from those listed at paragraph [0022] of US Patent Publication 2007/0207925, the contents of which are incorporated herein by reference in their entirety.

Aptly, the colour-forming species is chosen from crystal violet lactone, 2-(dibenzylamino)-6-(diethylamino)fluoran and 6-diethylamino-3-methyl-2-phenylaminofluoran. Trade names for the latter molecules are WinCon Green and WinCon-1 respectively (Connect Chemicals GmbH).

Aptly, the colour-forming species is a phthalide-based leuco dye having the following structure:

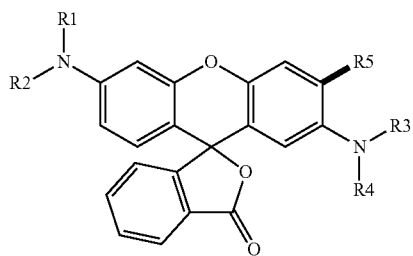

Aptly, R1 is a moiety selected from the group consisting of ethyl and butyl.

Aptly, R2 is a moiety selected from the group consisting of ethyl, butyl and isopentyl.

Aptly, R3 is a moiety selected from the group consisting of benzyl, phenyl and xylenyl.

Aptly, R4 is a moiety selected from the group consisting of benzyl and H.

Aptly, R5 is a moiety selected from the group consisting of H and methyl.

Aptly, R1 is ethyl, R2 is ethyl, R3 and R4 are benzyl and R5 is H.

Aptly, R1 and R2 are both ethyl, R3 is phenyl, R4 is H and R5 is methyl.

Aptly, R1 and R2 are both butyl, R3 is phenyl, R4 is H, and R5 is methyl.

Aptly, R1 and R2 are both ethyl, R3 is xylenyl, R4 is H and R5 is methyl.

Aptly, R1 is ethyl, R2 is isopentyl, R3 is phenyl, R4 is H and R5 is methyl.

The colour-forming species may be a single species or more than one of the colour-forming species listed herein and they may be applied to the HPU in combination with one another or separately, for example in discrete regions.

Aptly, the colour-forming species is substantially insoluble in water with a solubility of less than 1 mg per liter e.g. at 22.5° C. Aptly, the colour-forming species is substantially insoluble in water with a solubility of less than 0.1 mg per liter e.g. at 22.5° C.

Aptly, when the colour-forming species is crystal violet lactone, the presence of moisture is indicated by blue colouration.

Aptly, when the colour-forming species is 2-(dibenzylamino)-6-(diethylamino)fluoran, the presence of moisture is indicated by green colouration.

Aptly, when the colour-forming species is 6-diethylamino-3-methyl-2-phenylaminofluoran, the presence of moisture is indicated by black-grey colouration.

The intensity of the colour formed in the presence of moisture and the extent of the background colour in the absence of moisture can be adjusted by controlling the concentration of colour-forming species presented upon or within the HPU.

The colour-forming species is aptly applied in a solution to the HPU. In one embodiment, the CF solution is a non-aqueous solution and may, for example comprise organic or slightly polar solvents that include acetone, xylene, toluene, iso-propanol, ethanol and methanol or combinations thereof. The concentration of CF applied in solution varies depending upon the method of application but, for example, a suitable spray-coating or dip-coating can be achieved from CF solutions in the concentration range 0.01-100 mg/ml, e.g. 0.01-10 mg/ml.

The CF can be applied at loading levels of up to 10% w/w of the HPU. In practice, the dye loading level is aptly less than 1% w/w of the HPU. Aptly, the dye loading level is less than 0.1% w/w of the HPU.

The CF can be applied continuously or in a discrete pattern to the HPU. For some applications that involve the absorption of coloured liquid, a patterned indicator can be of benefit for unequivocal assessment of moisture level.

Accordingly, a further aspect of the present invention provides a process for the production of a material of the first aspect of this invention comprising:
(a) preparing a solution of a colour-forming species e.g. a colour-forming dye in a non-aqueous solvent;
(b) combining the solution with a hydrophilic polyurethane (HPU) (e.g. spray-coating, dipping or printing); and
(c) removing the non-aqueous solvent e.g. by heating or the application of reduced pressure, or both.

In one embodiment, step (c) comprises evaporating the solvent at ambient temperature (i.e. without heating).

Aptly, the HPU is a HPU foam.

The HPU foam may be prepared to its final thickness prior to its combination with colour-forming dye or may be impregnated in the bulk prior to slicing.

Aptly, the HPU and the colour-forming solution are combined by spray-coating, dipping and/or printing.

It is desirable in some instances that the solution of the colour-forming dye is applied to only the part or parts of the device available for visual inspection in the final product.

Step (b) is aptly achieved by a continuous process such as the surface coating of roll-stock in a reel-to-reel process. Surface coating is aptly achieved by kiss-coating, padding or spray-coating.

In one embodiment, removal of non-aqueous solvent comprises heating. Suitable heating mechanisms include oven, infra-red lamp, radio-frequency and microwave.

In one embodiment, there is provided a topical device for application to the skin of the user comprising the article of the first aspect of the invention.

The topical device can be any for application proximate to a source of liquid or a potential source of liquid. Suitable locations include natural or unnatural bodily orifices including, but not limited to, wounds and penetrating sites such as intra-venous line sites, ostomy sites, and catheters and drains sites. Aptly, the device comprises an article as described herein for the indication of the extent of moisture absorption within the device.

In one embodiment, the device is incorporated in a wound dressing. The wound dressing may comprise one or more further components e.g. anti-microbial components, adhesive components and the like.

Aptly, the device is incorporated into a post-operative device.

The device may be for use to treat a subject. The subject may be a human or an animal subject.

Aptly, the article or a device comprising the article is for the detection of humidity of a target location. In one embodiment, the article is for use in determining humidity levels in an environment. In one embodiment, the article can be used to visibly detect humidity levels of 80% or greater. Aptly, the article and/or device is for use to indicate environmental moisture conditions. In one embodiment, the article and/or device may be used to indicate environmental conditions conducive to moist wound healing. Embodiments of the present invention may have utility e.g. in controlled humidity transport systems. Aptly, the article and/or device can be used to alert a user when humidity levels are outside a desired parameter.

In one embodiment, the article and/or device is a product from rehabilitation therapy that comprises an element that is wet by the user prior to therapy and must be repeatedly squeezed to dryness during therapy, resulting in a colour change. Such an element may be a ball or suchlike or may, alternatively be a strip for topical application to a location on a body.

In one embodiment, the article and/or device is a toy item or novelty product e.g. a "stress-relief" toy which is squeezable by a user and which changes colour when the user's hand has moisture on it. The toy item may be sized and shaped in a variety of ways including e.g. to replicate items such as mobile telephones and the like. Aptly, the toy item may be a foam ball. Aptly, the article and/or device is a bath sponge or kitchen utensil e.g. a dish washing sponge utensil.

In one embodiment, the article and/or device is a target that indicates when it has been wet. This article and/or device may be worn by a user to indicate where and when they have been exposed to a water source, for example a water pistol jet or water bomb.

Aptly, the article and/or device is for use as a soil replacement device e.g. for use in a hydroponic system. Aptly, the soil replacement device is capable of indicating the moisture level of a hydroponic system and is therefore capable of alerting a user if and when more or less moisture is required.

Aptly, the article and/or device of the present invention is designed to get wet in use and therefore is capable of indicating that it is fulfilling that requirement. Aptly, component or device comprising the article described herein can be placed at an apt location in fluid-handling devices to indicate that the device is full (i.e. up to its maximum holding capacity). This location may be adjacent to an exit orifice of a water containment chamber (including those used for medical fluid drainage, including for example negative pressure wound therapy).

In one embodiment, the article is for incorporation into a sanitary product e.g. a diaper or other absorbent article. The article is able to indicate that the sanitary product is wet and therefore requires replacing.

In one embodiment, a device comprising an article as described herein may be a visual humidity indicator for humidity chambers e.g. saunas and steam rooms and laboratory incubators.

In one embodiment, the device is a visual indicator for indicating the dryness level of an environment.

In one embodiment, the article is for use as a skin hydration patch. Aptly, the article is capable of indicating whether a user's skin is suitably hydrated.

A further aspect of the present invention provides a device for the measurement of moisture content comprising the article or device of the present invention and a calibrated colour chart to enable the determination of moisture level in the device.

The colour chart is calibrated according to the desired range of moisture detection. For example, referring to FIG. 12, the colour chart is coloured with a series (e.g. 3-7 in number) of discrete coloured areas that correspond to specific moisture levels. The increments may be in 20% w/w moisture level steps for example. The colours (when printed) are matched to the actual colour of the device by measuring their light absorbance. Alternatively, the coloured areas may be generated by reproducing images of the actual device itself in a range of states of wetness.

A further aspect of the present invention provides a device for the measurement of moisture content comprising the article and/or device of the present invention and a spectrometer to enable the determination of moisture level in the device. The output of this device may be a numerical moisture level.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

There now follows a series of specific embodiments of the invention. These specific embodiments do not restrict the scope of the invention.

EXAMPLES

Example 1

Preparation of Crystal Violet Lactone Dip-Coated MDI-Based HPU Foam

A solution of crystal violet lactone in acetone (16 mg/ml) was prepared. A 20×20×5 mm square sample of a MDI-based HPU foam (Cutimed Cavity, BSN Ltd) was fully immersed in the crystal violet lactone solution (20 ml), taking care to avoid air-locking within the foam. The sample was immediately removed from the solution and excess solution removed with light squeezing followed by hand compression between layers of absorbent tissue. The sample was oven dried at 70° C. for 10 minutes, resulting in an off-white sample.

Example 2

Preparation of 2-dibenzylamino-6-diethylaminofluoran dip-coated MDI-based HPU foam A solution of 2-dibenzylamino-6-diethylaminofluoran in acetone (5 mg/ml) was prepared. A 20×20×5 mm square sample of a MDI-based HPU foam (Cutimed Cavity, BSN Ltd) was fully immersed in the 2-dibenzylamino-6-diethylaminofluoran solution (20 ml), taking care to avoid air-locking within the foam. The sample was immediately removed from the solution and excess solution removed with light squeezing followed by hand compression between layers of absorbent tissue. The sample was oven dried at 70° C. for 10 minutes, resulting in an off-white sample.

Example 3

Preparation of 6-diethylamino-3-methyl-2-phenylaminofluoran dip-coated MDI-based HPU foam A solution of 6-diethylamino-3-methyl-2-phenylaminofluoran in acetone (5 mg/ml) was prepared. A 20×20×5 mm square sample of a MDI-based HPU foam (Cutimed Cavity, BSN Ltd) was fully immersed in the 6-diethylamino-3-methyl-2-phenylaminofluoran solution (20 ml), taking care to avoid air-locking within the foam. The sample was immediately removed from the solution and excess solution removed with light squeezing followed by hand compression between layers of absorbent tissue. The sample was oven dried at 70° C. for 10 minutes, resulting in an off-white sample.

Example 4

Preparation of 6-dibutylamino-3-methyl-2-phenylaminofluoran dip-coated MDI-based HPU foam A solution of 6-dibutylamino-3-methyl-2-phenylaminofluoran in acetone (5 mg/ml) was prepared. A 20×20×5 mm square sample of a MDI-based HPU foam (Cutimed Cavity, BSN Ltd) was fully immersed in the 6-dibutylamino-3-methyl-2-phenylaminofluoran solution (20 ml), taking care to avoid air-locking within the foam. The sample was immediately removed from the solution and excess solution removed with light squeezing followed by hand compression between layers of absorbent tissue. The sample was oven dried at 70° C. for 10 minutes, resulting in an off-white sample.

Example 5

Preparation of 2-(dimethylphenylamino)-3-methyl-6-diethylaminofluoran dip-coated MDI-based HPU foam A solution of 2-(dimethylphenylamino)-3-methyl-6-diethylaminofluoran in acetone (5 mg/ml) was prepared. A 20×20×5 mm square sample of a MDI-based HPU foam (Cutimed Cavity, BSN Ltd) was fully immersed in the 2-(dimethylphenylamino)-3-methyl-6-diethylaminofluoran solution (20 ml), taking care to avoid air-locking within the foam. The sample was immediately removed from the solution and excess solution removed with light squeezing followed by hand compression between layers of absorbent tissue. The sample was oven dried at 70° C. for 10 minutes, resulting in an off-white sample.

Example 6

Preparation of 6-(N-ethyl,N-isopentylamino)-3-methyl-2-phenylaminofluoran dip-coated MDI-based HPU foam A solution of 6-(N-ethyl,N-isopentylamino)-3-methyl-2-phenylaminofluoran in acetone (5 mg/ml) was prepared. A 20×20×5 mm square sample of a MDI-based HPU foam (Cutimed Cavity, BSN Ltd) was fully immersed in the 6-(N-ethyl,N-isopentylamino)-3-methyl-2-phenylaminofluoran solution (20 ml), taking care to avoid air-locking within the foam. The sample was immediately removed from the solution and excess solution removed with light squeezing followed by hand compression between layers of absorbent tissue. The sample was oven dried at 70° C. for 10 minutes, resulting in an off-white sample.

Example 7

Preparation of Crystal Violet Lactone Spray-Coated MDI-Based HPU Foam

A solution (50 ml) of crystal violet lactone in acetone (16 mg/ml) was prepared and loaded into an atomising hand-sprayer. A 100×100×5 mm square sample of a MDI-based HPU foam (Cutimed Cavity, BSN Ltd) was positioned upon a flat polypropylene sheet. The foam was sprayed uniformly with the crystal violet lactone solution and immediately oven dried at 70° C. for 10 minutes resulting in an off-white sample.

Example 8

Preparation of 2-dibenzylamino-6-diethylaminofluoran spray-coated MDI-based HPU foam A solution (50 ml) of 2-dibenzylamino-6-diethylaminofluoran in acetone (5 mg/ml) was prepared and loaded into an atomising hand-sprayer. A 100×100×5 mm square sample of a MDI-based HPU foam (Cutimed Cavity, BSN Ltd) was positioned upon a flat polypropylene sheet. The foam was sprayed uniformly with the 2-dibenzylamino-6-diethylaminofluoran solution and immediately oven dried at 70° C. for 10 minutes resulting in an off-white sample.

Example 9

Preparation of 6-diethylamino-3-methyl-2-phenylaminofluoran spray-coated MDI-based HPU foam A solution (50 ml) of 6-diethylamino-3-methyl-2-phenylaminofluoran in acetone (5 mg/ml) was prepared and loaded into an atomising hand-sprayer. A 100×100×5 mm square sample of a MDI-based HPU foam (Cutimed Cavity, BSN Ltd) was positioned upon a flat polypropylene sheet. The foam was sprayed uniformly with the 6-diethylamino-3-methyl-2-phenylaminofluoran solution and immediately oven dried at 70° C. for 10 minutes resulting in an off-white sample.

Example 10

Preparation of Crystal Violet Lactone Pattern Spray-Coated MDI-Based HPU Foam

A solution (50 ml) of crystal violet lactone in acetone (16 mg/ml) was prepared and loaded into an atomising hand-sprayer. A 100×100×5 mm square sample of a MDI-based HPU foam (Cutimed Cavity, BSN Ltd) was positioned upon a flat polypropylene sheet. An aluminium masking sheet with circular apertures of 4 mm in diameter (arranged in a uniform hexagonal array with centre-to-centre spacing of 8 mm) was placed upon the foam. The foam was sprayed uniformly with the crystal violet lactone solution and mask removed prior to immediately oven drying at 70° C. for 10 minutes resulting in an off-white patterned sample.

Example 11

Preparation of 2-dibenzylamino-6-diethylaminofluoran pattern spray-coated MDI-based HPU foam A solution (50 ml) of 2-dibenzylamino-6-diethylaminofluoran in acetone (5 mg/ml) was prepared and loaded into an atomising hand-sprayer. A 100×100×5 mm square sample of a MDI-based HPU foam (Cutimed Cavity, BSN Ltd) was positioned upon a flat polypropylene sheet. An aluminium masking sheet with circular apertures of 4 mm in diameter (arranged in a uniform hexagonal array with centre-to-centre spacing of 8 mm) was placed upon the foam. The foam was sprayed uniformly with the 2-dibenzylamino-6-diethylaminofluoran solution and mask removed prior to immediately oven drying at 70° C. for 10 minutes resulting in an off-white patterned sample.

Example 12

Preparation of 6-diethylamino-3-methyl-2-phenylaminofluoran pattern spray-coated MDI-based HPU foam A solution (50 ml) of 6-diethylamino-3-methyl-2-phenylaminofluoran in acetone (5 mg/ml) was prepared and loaded into an atomising hand-sprayer. A 100×100×5 mm square sample of a MDI-based HPU foam (Cutimed Cavity, BSN Ltd) was positioned upon a flat polypropylene sheet. An aluminium masking sheet with circular apertures of 4 mm in diameter (arranged in a uniform hexagonal array with centre-to-centre spacing of 8 mm) was placed upon the foam. The foam was sprayed uniformly with the 6-diethylamino-3-methyl-2-phenylaminofluoran solution and mask removed prior to immediately oven drying at 70° C. for 10 minutes resulting in an off-white patterned sample.

Example 13

Preparation of Crystal Violet Lactone Dip-Coated TDI-Based HPU Foam

A solution of crystal violet lactone in acetone (16 mg/ml) was prepared. A 20×20×5 mm square sample of a TDI-based HPU foam (Allevyn, Smith & Nephew Medical Ltd) was fully immersed in the crystal violet lactone solution (20 ml), taking care to avoid air-locking within the foam. The sample was immediately removed from the solution and excess solution removed with light squeezing followed by hand compression between layers of absorbent tissue.
The sample was oven dried at 70° C. for 10 minutes, resulting in an off-white sample.

Example 14

Preparation of 2-dibenzylamino-6-diethylaminofluoran dip-coated TDI-based HPU foam A solution of 2-dibenzylamino-6-diethylaminofluoran in acetone (5 mg/ml) was prepared. A 20×20×5 mm square sample of a TDI-based HPU foam (Allevyn, Smith & Nephew Medical Ltd) was fully immersed in the 2-dibenzylamino-6-diethylaminofluoran solution (20 ml), taking care to avoid air-locking within the foam. The sample was immediately removed from the solution and excess solution removed with light squeezing followed by hand compression between layers of absorbent tissue. The sample was oven dried at 70° C. for 10 minutes, resulting in an off-white sample.

Example 15

Preparation of 6-diethylamino-3-methyl-2-phenylaminofluoran dip-coated TDI-based HPU foam A solution of 6-diethylamino-3-methyl-2-phenylaminofluoran in acetone (5 mg/ml) was prepared. A 20×20×5 mm square sample of a TDI-based HPU foam (Allevyn, Smith & Nephew Medical Ltd) was fully immersed in the 6-diethylamino-3-methyl-2-phenylaminofluoran solution (20 ml), taking care to avoid air-locking within the foam. The sample was immediately removed from the solution and excess solution removed with light squeezing followed by hand compression between layers of absorbent tissue. The sample was oven dried at 70° C. for 10 minutes, resulting in an off-white sample.

Example 16

Preparation of 6-dibutylamino-3-methyl-2-phenylaminofluoran dip-coated TDI-based HPU foam A solution of 6-dibutylamino-3-methyl-2-phenylaminofluoran in acetone (5 mg/ml) was prepared. A 20×20×5 mm square sample of a TDI-based HPU foam (Allevyn, Smith & Nephew Medical Ltd) was fully immersed in the 6-dibutylamino-3-methyl-2-phenylaminofluoran solution (20 ml), taking care to avoid air-locking within the foam. The sample was immediately removed from the solution and excess solution removed with light squeezing followed by hand compression between layers of absorbent tissue. The sample was oven dried at 70° C. for 10 minutes, resulting in an off-white sample.

Example 17

Preparation of 2-(dimethylphenylamino)-3-methyl-6-diethylaminofluoran dip-coated TDI-based HPU foam A solution of 2-(dimethylphenylamino)-3-methyl-6-diethylaminofluoran in acetone (5 mg/ml) was prepared. A 20×20×5 mm square sample of a TDI-based HPU foam (Allevyn, Smith & Nephew Medical Ltd) was fully immersed in the 2-(dimethylphenylamino)-3-methyl-6-diethylaminofluoran solution (20 ml), taking care to avoid air-locking within the foam. The sample was immediately removed from the solution and excess solution removed with light squeezing followed by hand compression between layers of absorbent tissue. The sample was oven dried at 70° C. for 10 minutes, resulting in an off-white sample.

Example 18

Preparation of 6-(N-ethyl,N-isopentylamino)-3-methyl-2-phenylaminofluoran dip-coated TDI-based HPU foam A solution of 6-(N-ethyl,N-isopentylamino)-3-methyl-2-phenylaminofluoran in acetone (5 mg/ml) was prepared. A 20×20×5 mm square sample of a TDI-based HPU foam (Allevyn, Smith & Nephew Medical Ltd) was fully immersed in the 6-(N-ethyl,N-isopentylamino)-3-methyl-2-phenylaminofluoran solution (20 ml), taking care to avoid air-locking within the foam. The sample was immediately removed from the solution and excess solution removed with light squeezing followed by hand compression between layers of absorbent tissue. The sample was oven dried at 70° C. for 10 minutes, resulting in an off-white sample.

Example 19

Preparation of Crystal Violet Lactone Spray-Coated TDI-Based HPU Foam

A solution (50 ml) of crystal violet lactone in acetone (16 mg/ml) was prepared and loaded into an atomising hand-sprayer. A 100×100×5 mm square sample of a TDI-based HPU foam (Allevyn, Smith & Nephew Medical Ltd) was positioned upon a flat polypropylene sheet. The foam was sprayed uniformly with the crystal violet lactone solution and immediately oven dried at 70° C. for 10 minutes resulting in an off-white sample.

Example 20

Preparation of 2-dibenzylamino-6-diethylaminofluoran spray-coated TDI-based HPU foam A solution (50 ml) of 2-dibenzylamino-6-diethylaminofluoran in acetone (5 mg/ml) was prepared and loaded into an atomising hand-sprayer. A 100×100×5 mm square sample of a TDI-based HPU foam (Allevyn, Smith & Nephew Medical Ltd) was positioned upon a flat polypropylene sheet. The foam was sprayed uniformly with the 2-dibenzylamino-6-diethylaminofluoran solution and immediately oven dried at 70° C. for 10 minutes resulting in an off-white sample.

Example 21

Preparation of 6-diethylamino-3-methyl-2-phenylaminofluoran spray-coated TDI-based HPU foam A solution (50 ml) of 6-diethylamino-3-methyl-2-phenylaminofluoran in acetone (5 mg/ml) was prepared and loaded into an atomising hand-sprayer. A 100×100×5 mm square sample of a TDI-based HPU foam (Allevyn, Smith & Nephew Medical Ltd) was positioned upon a flat polypropylene sheet. The foam was sprayed uniformly with the 6-diethylamino-3-methyl-2-phenylaminofluoran solution and immediately oven dried at 70° C. for 10 minutes resulting in an off-white sample.

Example 22

Preparation of Crystal Violet Lactone Pattern Spray-Coated TDI-Based HPU Foam

A solution (50 ml) of crystal violet lactone in acetone (16 mg/ml) was prepared and loaded into an atomising hand-sprayer. A 100×100×5 mm square sample of a TDI-based HPU foam (Allevyn, Smith & Nephew Medical Ltd) was positioned upon a flat polypropylene sheet. An aluminium masking sheet with circular apertures of 4 mm in diameter (arranged in a uniform hexagonal array with centre-to-centre spacing of 8 mm) was placed upon the foam. The foam was sprayed uniformly with the crystal violet lactone solution and mask removed prior to immediately oven drying at 70° C. for 10 minutes resulting in an off-white patterned sample.

Example 23

Preparation of 2-dibenzylamino-6-diethylaminofluoran pattern spray-coated TDI-based HPU foam A solution (50 ml) of 2-dibenzylamino-6-diethylaminofluoran in acetone (5 mg/ml) was prepared and loaded into an atomising hand-sprayer. A 100×100×5 mm square sample of a TDI-based HPU foam (Allevyn, Smith & Nephew Medical Ltd) was positioned upon a flat polypropylene sheet. An aluminium masking sheet with circular apertures of 4 mm in diameter (arranged in a uniform hexagonal array with centre-to-centre spacing of 8 mm) was placed upon the foam. The foam was sprayed uniformly with the 2-dibenzylamino-6-diethylaminofluoran solution and mask removed prior to immediately oven drying at 70° C. for 10 minutes resulting in an off-white patterned sample.

Example 24

Preparation of 6-diethylamino-3-methyl-2-phenylaminofluoran pattern spray-coated TDI-based HPU foam A solution (50 ml) of 6-diethylamino-3-methyl-2-phenylaminofluoran in acetone (5 mg/ml) was prepared and loaded into an atomising hand-sprayer. A 100×100×5 mm square sample of a TDI-based HPU foam (Allevyn, Smith & Nephew Medical Ltd) was positioned upon a flat polypropylene sheet. An aluminium masking sheet with circular apertures of 4 mm in diameter (arranged in a uniform hexagonal array with centre-to-centre spacing of 8 mm) was placed upon the foam. The foam was sprayed uniformly with the 6-diethylamino-3-methyl-2-phenylaminofluoran solution and mask removed prior to immediately oven drying at 70° C. for 10 minutes resulting in an off-white patterned sample.

Example 25

Determination of the Magnitude of Colour Change in Presence and Absence of Moisture for a Range of Colour-Formers Dip-Coated on MDI and TDI HPU Foam A range of colour-formers were dip-coated onto MDI- and TDI-based HPU foams using the following method:

A solution of colour-former in acetone (5 mg/ml) was prepared. A 20×20×5 mm square sample of a TDI-based or MDI-based HPU foam was fully immersed in the colour-former solution (20 ml), taking care to avoid air-locking within the foam. The sample was immediately removed from the solution and excess solution removed with light squeezing followed by hand compression between layers of absorbent tissue.

The sample was oven dried at 70° C. for 10 minutes, resulting in an off-white sample in all cases.

The light absorbance of the resulting samples was recorded in the dry state at the wavelength of maximum light absorbance (when moistened). Each sample was individually fully wet out in deionised water and dried to dampness between absorbent tissue prior to immediate determination of light absorbance at the aforementioned wavelength.

The colour formers, HPU foam type, light absorbance wavelength and light absorbances in the dry and damp state are tabulated below. The colour formers were purchased from Connect Chemicals GmbH, with the exception of crystal violet lactone, and below are named using their trade-names:

| Trade Name | Chemical | CAS |
|---|---|---|
| Pergascript Yellow I 3R | 4,4'-[(1-methylethylidene)bis(4,1-phenyleneoxy-4,2-quinazolinediyl)]bis[N,N-diethyl]benzamine | 90677-64-8 |
| WinCon Red | 3,3-bis(N-octyl-2-methyl indole)phthalide | 50292-95-0 |
| WinCon Green | 2-dibenzylamino-6-diethylaminofluoran | 34372-72-0 |
| WC1 | 6-diethylamino-3-methyl-2-phenylaminofluoran | 29512-49-0 |
| WC2 | 6-dibutylamino-3-methyl-2-phenylaminofluoran | 89331-94-2 |
| WC15 | 2-(2,4-dimethylphenylamino)-3-methyl-6-diethylaminofluoran | 72389-80-1 |
| WC205 | 6-(N-ethyl, N-isopentylamino)-3-methyl-2-phenylaminofluoran | 70516-41-5 |

| HPU foam | Colour-former | State | Wavelength of absorbance | Absorbance | Enhancement |
|---|---|---|---|---|---|
| MDI | Pergascript Yellow I 3R | dry | 452 | 0.086 | |
| MDI | | damp | 452 | 0.094 | 1.1 |
| MDI | WinCon Red | dry | 538 | 0.018 | |
| MDI | | damp | 538 | 0.063 | 3.5 |
| MDI | Crystal Violet Lactone | dry | 607 | 0.023 | |
| MDI | | damp | 607 | 0.308 | 13.4 |
| MDI | WinCon Green | dry | 600 | 0.142 | |
| MDI | | damp | 600 | 0.806 | 5.7 |
| MDI | WinCon-1 | dry | 600 | 0.216 | |
| MDI | | damp | 600 | 1.338 | 6.2 |
| MDI | WinCon-2 | dry | 600 | 0.137 | |
| MDI | | damp | 600 | 0.786 | 5.7 |
| MDI | WinCon-15 | dry | 600 | 0.181 | |
| MDI | | damp | 600 | 1.236 | 6.8 |
| MDI | WinCon-205 | dry | 600 | 0.154 | |
| MDI | | damp | 600 | 0.975 | 6.3 |
| TDI | Pergascript Yellow I 3R | dry | 452 | 0.064 | |
| TDI | | damp | 452 | 0.046 | 0.7 |
| TDI | WinCon Red | dry | 538 | 0.015 | |
| TDI | | damp | 538 | 0.035 | 2.3 |
| TDI | Crystal Violet Lactone | dry | 607 | 0.019 | |
| TDI | | damp | 607 | 0.282 | 14.8 |
| TDI | WinCon Green | dry | 600 | 0.108 | |
| TDI | | damp | 600 | 0.761 | 7.0 |
| TDI | WinCon-1 | dry | 600 | 0.189 | |
| TDI | | damp | 600 | 1.294 | 6.8 |
| TDI | WinCon-2 | dry | 600 | 0.096 | |
| TDI | | damp | 600 | 0.781 | 8.1 |
| TDI | WinCon-15 | dry | 600 | 0.126 | |
| TDI | | damp | 600 | 1.166 | 9.3 |
| TDI | WinCon-205 | dry | 600 | 0.101 | |
| TDI | | damp | 600 | 1.042 | 10.3 |

These results are presented graphically in FIGS. 8 and 9.

FIG. 8 shows the light absorbances resulting from damp samples. In general, light absorbances exceeding 0.1 absorbance unit are observable to the average human. Thus WinCon Red and Pergascript Yellow I 3R are not well-suited to function as colour-forming indicators on MDI or TDI HPU foams in certain embodiments of the invention at the loading concentrations employed.

FIG. 9 shows the light absorbance enhancement that results when samples are wet from dryness. Excluding WinCon Red and Pergascript Yellow I 3R (see above), light absorbance enhancements are above 4-fold for the remaining colour-formers. This magnitude of colour change is visually striking and can easily be observed by the average human.

Example 26

Demonstration of the insolubility of 2-dibenzylamino-6-diethylaminofluoran

The material produced in Example 2 was immersed in 50 ml deionised water and fully wet out. Each day for 7 days, the sample was removed from the liquid, dried to dampness between absorbent tissue and its light absorbance was recorded at 600 nm. The sample was then re-immersed in a fresh 50 ml of deionised water. The resulting light absorbances are plotted in FIG. 10. This data illustrates that there is no loss in colour intensity over 7 days and this demonstrates that the colour-former is not being solubilised from the HPU foam.

Example 27

Investigation of the Relationship Between Dry and Wet Colour Intensity and Colour-Former Loading Different applications may require the development of different wet colour-intensity and electronic colour determination can be achieved at low levels that the average human cannot perceive. The sample preparation method performed in Example 2 was repeated (again using 2-dibenzylamino-6-diethylaminofluoran as the colour-former) with dip solution concentrations of 0-1 mg/ml. The dry and wet light absorbance of these samples was recorded at 600 nm and the resulting data plotted in FIG. 11. This data demonstrates that wet colour intensity can be varied in a predictable manner with colour-former loading solution concentration and also that, in the concentration range investigated, the dry colour intensity is not significantly different to untreated HPU to the average human (i.e. has a light absorbance below 0.1 absorbance unit).

Example 28

Measurement of Colour Response to Moisture of Crystal Violet Lactone Dip-Coated MDI-Based HPU Foam Prepared in Example 1

The crystal violet lactone-coated foam prepared in Example 1 was full immersed in deionised water, taking care to avoid air-locking within the foam. The foam immediately turned strongly blue in colour. No blue colour was observed in the water. The foam was removed from the water and excess water removed by light hand pressure between layers of absorbent tissue. The foam contained approximately 200% of its own weight in water after this process.

The weight and light absorbance at 610 nm of this damp foam were immediately recorded. The sample was then incubated at 30° C. and the light absorbance and weight of the sample was recorded for several hours after wetting. The results are shown in FIG. 12 and demonstrate a linear colour response to moisture level in the range 0-140% w/w.

Example 29

Gamma sterilisation stability of 2-dibenzylamino-6-diethylaminofluoran spray-coated MDI-based HPU foam The 2-dibenzylamino-6-diethylaminofluoran spray-coated MDI-based HPU foam prepared in Example 8 was cut into 2×2 cm samples and each sample was sealed inside a PET-PE pouch suitable for the long-term storage of medical devices. The devices were sterilised by gamma irradiation and aged at 25° C. and 40° C. in a controlled environmental chamber. The dry colour and humidity-indicating response was not attenuated by sterilisation or storage at 25° C. or 40° C. for 12 months.

Example 30

Ethylene oxide sterilisation stability of 2-dibenzylamino-6-diethylaminofluoran spray-coated MDI-based HPU foam The 2-dibenzylamino-6-diethylaminofluoran spray-coated MDI-based HPU foam prepared in Example 8 was cut into 2×2 cm samples and each sample was sealed inside a paper-PE pouch suitable for the long-term storage of medical devices. The devices were sterilised by ethylene oxide treatment and aged at 25° C. and 40° C. in a controlled environmental chamber. The dry colour and humidity-indicating response was not attenuated by sterilisation or storage at 25° C. or 40° C. for 12 months.

Example 31

Preparation of Moisture-Indicating HPU Powder for Incorporation onto or into Other Materials The moisture indicating HPU foam materials produced in Examples 1 and 2 were cryo-milled to powders of average particle size 100 microns and dried prior to storage. The powders maintained the moisture-indicating property of their parent HPU foams and are suitable for incorporation onto or into other materials for the purpose of moisture indication.

As described herein, certain embodiments of the present invention relate to solid and/or molecular dispersions of a colour-forming species in a hydrophilic polyurethane foam. In this respect, certain embodiments of the present invention relate to the application of a colour-forming species to the hydrophilic polyurethane foam in an organic solvent. Example 32 below demonstrates a lack of moisture indicating property in a macroscopic mixture of hydrophilic polyurethane foam and the colour-former crystal violet lactone.

Example 32

2×2 cm samples of MDI-based and TDI-based HPU foam were brushed with a coating of crystal violet lactone powder. Excess powder was removed from the sample. Each sample was immersed individually in excess deionised water, resulting in no colour change.

The samples produced in Example 32 are macroscopic mixtures of colour former and HPU formed from a solid material comprising the colour forming species and do not function as moisture indicators.

The invention claimed is:

1. An article for indicating presence of moisture comprising a material comprising a hydrophilic polyurethane and a colour-forming species,
    wherein the material does not comprise an excipient that is soluble in aqueous media,
    wherein the hydrophilic polyurethane is formed from a composition comprising at least 1% by weight of a methyl diphenyl diisocyanate (MDI)-based prepolymer, or
    wherein the hydrophilic polyurethane is formed from a composition comprising at least 1% by weight of a toluene diisocyanate (TDI)-based prepolymer, and
    wherein the colour-forming species is a molecule which can exist in at least two coloured states, wherein the colour-forming species exists in one of the coloured states when in contact with moisture.

2. The article according to claim 1, wherein the colour-forming species is a solid dispersion in the hydrophilic polyurethane.

3. The article according to claim 1, wherein the colour-forming species is a molecular dispersion or partial molecular dispersion in the hydrophilic polyurethane.

4. The article according to claim 1, wherein the hydrophilic polyurethane is a hydrophilic polyurethane foam.

5. The article according to claim 1, wherein one or both of the hydrophilic polyurethane and the colour-forming species is substantially insoluble in an aqueous media.

6. The article according to claim 1, wherein the MDI-based prepolymer comprises 10-90% by weight of MDI.

7. The article according to claim 1, wherein the TDI-based prepolymer comprises 10-90% by weight of TDI.

8. The article according to claim 1, wherein one of the coloured states is a colourless state.

9. The article according to claim 1, wherein the colour-forming species is a colour-forming dye.

10. The article according to claim 9, wherein the colour-forming dye is a phthalide-based leuco dye.

11. The article according to claim 9, wherein the colour-forming dye is crystal violet lactone.

12. The article according to claim 9, wherein the colour-forming dye is 2 dibenzylamino-6-diethylaminofluoran.

13. The article according to claim 9, wherein the colour-forming dye is 6-diethylamino-3-methyl-2-phenylaminofluoran.

14. The article according to claim 9, wherein the colour-forming dye is 6-dibutylamino-3-methyl-2-phenylaminofluoran.

15. The article according to claim 9, wherein the colour-forming dye is 2 (dimethylphenylamino)-3-methyl-6-diethylaminofluoran.

16. The article according to claim 9, wherein the colour-forming dye is 6-(N-ethyl,N-isopentylamino)-3-methyl-2-phenylaminofluoran.

17. The article according to claim 1, wherein the article comprises a plurality of colour-forming species.

18. The article according to claim 17, wherein each colour-forming species of the plurality of colour-forming species are provided in discrete regions of the article.

19. The article according to claim 1, wherein the colour forming species is loaded onto the hydrophilic polyurethane at a level of about 10% w/w or lower.

20. The article according to claim 19, wherein the colour-forming species is loaded onto the hydrophilic polyurethane at a level of about 1% w/w or lower.

21. The article according to claim 1, wherein the colour-forming species is provided localized to the surface region of the hydrophilic polyurethane.

22. The article according to claim 21, wherein the article comprises a pattern comprising the colour-forming species.

23. A device for indicating the presence of moisture at a site, wherein the device comprises an article according to claim 1.

24. The device according to claim 23, wherein the device is for topical application to a site on a subject.

25. The device according to claim 24, wherein the device further comprises a protective layer on a surface thereof.

26. The device according to claim 25, wherein the protective layer is provided adjacent to the surface on which the colour-forming species is coated.

27. The device according to claim 23, wherein the device is for medical use.

28. The device according to claim 23, wherein the device is adapted to be applied to a wound or other penetrating site.

29. A method of manufacturing an article according to claim 1, wherein the method comprises:
    a) forming a solution of a colour-forming species in a non-aqueous solvent;
    b) combining the solution of (a) with a hydrophilic polyurethane; and
    c) removing the non-aqueous solvent.

30. The method according to claim 29, wherein combining the solution with a hydrophilic polyurethane comprises spray-coating, padding, dipping and/or printing.

31. The method according to claim 29, wherein removing the non-aqueous solvent comprises heating the article and/or applying a reduced pressure thereto.

32. The method according to claim 29, wherein the non-aqueous solvent is selected from an organic solvent and a slightly polar solvent.

33. The method according to claim 32, wherein the non-aqueous solvent is selected from acetone, xylene, toluene, iso-propanol, ethanol and methanol or combinations of these.

* * * * *